United States Patent [19]

Ullman et al.

[11] 4,065,354

[45] * Dec. 27, 1977

[54] LYSOZYME CONJUGATES FOR ENZYME IMMUNOASSAYS

[75] Inventors: Edwin F. Ullman, Atherton; Kenneth E. Rubenstein, Menlo Park, both of Calif.

[73] Assignee: Syva Company, Palo Alto, Calif.

[ * ] Notice: The portion of the term of this patent subsequent to Sept. 16, 1992, has been disclaimed.

[21] Appl. No.: 615,152

[22] Filed: Sept. 19, 1975

Related U.S. Application Data

[63] Continuation-in-part of Ser. No. 513,662, Oct. 10, 1974, Pat. No. 3,905,871, and Ser. No. 481,022, June 20, 1974, abandoned, each is a continuation-in-part of Ser. No. 143,609, May 14, 1971, abandoned.

[51] Int. Cl.² ........................ G01N 31/14; C07G 7/02
[52] U.S. Cl. ................................ 195/63; 195/103.5 R

[58] Field of Search .......................................... 195/63

[56] References Cited

U.S. PATENT DOCUMENTS

| | | | |
|---|---|---|---|
| 3,852,157 | 12/1974 | Rubenstein et al. | 195/63 |
| 3,867,366 | 2/1975 | Rubenstein et al. | 195/63 |
| 3,905,871 | 9/1975 | Rubenstein et al. | 195/63 |

*Primary Examiner*—Alvin E. Tanenholtz
*Attorney, Agent, or Firm*—Townsend and Townsend

[57] ABSTRACT

Novel conjugated enzyme compositions are provided for use in homogeneous immunoassays. A wide variety of haptenic compounds, such as drugs of abuse, therapeutic drugs, naturally occurring hormones, and the like, are conjugated to the enzyme lysozyme for use as reagents in homogeneous enzyme immunoassays. From 1 to 5 haptens are conjugated to the enzyme, and the enzyme is substantially inhibited when bound to antibodies bound to the conjugated hapten.

12 Claims, No Drawings

LYSOZYME CONJUGATES FOR ENZYME IMMUNOASSAYS

CROSS REFERENCE TO RELATED APPLICATIONS

This application is a continuation-in-part of application Ser. No. 513,662, filed Oct. 10, 1974, now U.S. Pat. No. 3,905,871; and Ser. No. 481,022, filed June 20, 1974, now abandoned; which are in turn continuation-in-part applications of Ser. No. 143,609, filed May 14, 1971, now abandoned.

BACKGROUND OF THE INVENTION

1. Field of the Invention

Immunoassays have shown themselves to be extremely versatile in allowing for methods to determine the presence of a particular substance, even when a wide variety of other materials of similar or different structure are present in the unknown sample. The immunoassays rely on the ability of an antibody to specifically detect or bind to an haptenic organic compound, while not interacting with other compounds. The divalent nature of the antibody and its high molecular weight, 150,000 or greater, allow for a sufficient change in the compound or environment of the compound to permit a discrimination between a compound which is bound and a compound which is not bound to antibody. Among various immunoassays involving antibodies are radioimmunoassay, spin immunoassays, reagents for which are available under the trademark FRAT, supplied by Syva Company; homogeneous enzyme immunoassay, reagents for which are available under the trademark EMIT, supplied by Syva Company; and hemeagglutination.

The enzyme immunoassay is extremely versatile in permitting spectrophotometric determinations. The immunoassay employs an enzyme to which the organic compound to be determined is conjugated. The organic compound is conjugated at a position where, when bound to antibody, the activity of the enzyme is substantially reduced. To the extent that the unknown sample contains the same organic compound, the amount of antibody available for binding to the organic compound conjugated to the enzyme is reduced. Therefore, by analyzing for enzymatic activity, a significant increase in enzymatic activity over the enzymatic activity in the absence of the unknown indicates the presence of the organic compound in the unknown.

The sensitivity of the homogeneous enzyme immunoassay is based to a substantial degree on the activity of the enzyme when conjugated and the degree of inhibitability when antibody is bound to the organic compound conjugated to the enzyme. It is, therefore, desirable to have an enzyme which not only has a high turnover rate initially, but retains a substantial proportion of this high turnover rate after conjugation, and is strongly inhibited when antibody is bound to the organic compound which is conjugated to the enzyme. Also, the enzyme should allow for strong specific binding of antibody to the conjugated organic compound.

DESCRIPTION OF THE PRIOR ART

An homogeneous enzyme immunoassay system has been sold under the trademark EMIT employing haptens conjugated to lysozyme, where the enzymatic activity is determined by the reduction in turbidity as a result of lysis of bacterial walls. Numerous publications concerning the system have issued since June 1971, see, for example, Rubenstein, et al., Biochem. and Biophysical Res. Comm., 47, 846 (1972). U.S. Pat. No. 3,654,090 teaches a heterogeneous immunoassay employing such enzymes as peroxidase and amyloglucosidase.

SUMMARY OF THE INVENTION

Haptenic conjugates to lysozyme are provided for employment in homogeneous enzyme immunoassays which provide high sensitivity in detecting extremely small amounts of organic materials. One or more of the haptens (hereinafter referred to as "ligands") are conjugated by relatively short chains or linking groups to lysozyme to provide a product retaining a substantial proportion of the original enzyme activity, which is greatly reduced when the conjugated hapten is bound to antibody. The linking chains normally employ non-oxo-carbonyl groups, although other covalent linking groups may also be employed.

DESCRIPTION OF THE SPECIFIC EMBODIMENTS

Haptenic conjugated lysozyme is provided having from about 1 to 5, usually from about 2 to 4 ligands, normally the majority of all the ligands being bonded to amino groups, particularly of lysine. The haptens or ligands will normally have molecular weights of at least 125, and generally not exceeding 1,000, more usually not exceeding 800, and frequently not exceeding 600 molecular weight. The ligands will have at least one heteroatom and may have two or more heteroatoms, which will normally be oxygen, nitrogen and sulfur, although halogen, particularly chlorine and iodine may also be present. The ligands for the most part will be naturally occurring, physiologically active compounds and synthetic drugs, which will be modified to the extent necessary for conjugation to the lysozyme. The haptens will include compounds having phenethylamine functionalities, heterocycles with one to two annular heteroatoms, particularly O and N and rings of from 6 to 7 annular members, having from 1 to 4 rings both fused and unfused.

The enzyme conjugates of this invention will for the most part have the following formula:

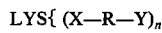

LYS(X—R—Y)$_n$ wherein:
  LYS intends lysozyme;
  $n$ indicates the average number of groups bonded to the LYS, and will generally be in the range of 1 to 5, more usually in the range of 2 to 5;
  R is a bond or a hydrocarbon (aliphatic, alicyclic aromatic, or combinations thereof), particularly aliphatic, linking group, either branched or straight chain, of from 0 to 1 rings and of from 1 to 12 carbon atoms, usually 1 to 8 carbon atoms, more usually of from 1 to 6 carbon atoms, and preferably of from 1 to 4 carbon atoms, usually having from 0 to 1 site of aliphatic unsaturation, and more usually aliphatically saturated, or substituted hydrocarbon group having from 0 to 3 heteroatoms, more usually 0 to 2 heteroatoms, which are oxygen, sulfur and nitrogen, more usually oxygen and nitrogen (atomic number 7 to 8), usually having from 0 to 1 heteroatoms in the chain, particularly oxy and tert.-amino; oxygen being present as oxy and oxo, particularly non-oxo-carbonyl; and Y is a ligand of at least 125 molecular weight, usually not greater than 1,200 molecular weight, more usually not greater than 1,000 molecular weight, and generally not exceeding 600 molecular weight, and has at least one common epitope to a naturally occurring physiologically active compound or synthetic drug, usually differing from the naturally occurring physiologically active compound or synthetic drug by replacement of a hydrogen or modification of a functionality such as an olefin, oxo or the like, to provide a site for bonding of R to the ligand; and X is a bond, a non-oxo-carbonyl group, including the nitrogen and sulfur analogs thereof, i.e. imino and thiocarbonyl, or diazo when R is arylene, aralkylene or a bond and the nitrogen of the diazo group is bonded to an aromatic annular carbon atom.

X may be bonded to R through carbon or a heteroatom, particularly nitrogen. Since sulfur bonds and certain oxygen bonds, e.g. ester, will tend to be reactive, these will usually be avoided. Oxygen will normally be present in the linking group as a carbonyl (oxo or non-oxo) or oxyether. Nitrogen will normally be present in the linking group as tertiary or quaternary amino, diazo or bonded to a non-oxo-carbonyl, including the amino and thioanalogs thereof.

Usually when R is aromatic (aromatic includes arylene, aralkylene or alkarylene), R will be bonded to Y through a heteroatom, particularly ethereal oxygen, i.e. oxy. R groups of particular interest are methylene or polymethylene, i.e. $(CH_2)_p$, where $p$ is an integer in the range of 1 to 6, alkyleneoxyalkylene, i.e. $(CH_2)_qO(CH_2)_r$, where $q$ and $r$ are the same or different and are integers in the range of 1 to 3, there being at least two methylene groups between heteroatoms, or $(CH_2)_sNH$, where $s$ is an integer in the range of 1 to 6 usually 1 to 4, there being at least two methylene groups between heteroatoms.

When X is other than a bond, X will normally have one of the following formulae:

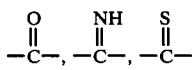

and will preferably be either the oxygen or the imino non-oxo-carbonyl.

The groups for —R—X will include ethylene, propylene, butylene, hexylene, phenylene, p-benzylylene, α-carboxymethine, carbamoylmethylene (—NHCOCH$_2$—), iminoxyacetyl (=NOCH$_2$CO—), thioacetyl, p-oxybenzyl, maledioyl, succindioyl, oxoethylene (—OCCH$_2$—), 1-oxobutylene(—OCCH$_2$CH$_2$CH$_2$), ethyleneoxyacetyl, propyleneoxyacetyl, N-methyl 3-aza-1-iminohexylene(—(NH=•C)—CH$_2$N(CH$_3$)CH$_2$CH$_2$CH$_2$—), ethylenecarbamoyl (—(O=C)NHCH$_2$CH$_2$—) propylenethiocarbamoyl (—(S—C)NHCH$_2$CH$_2$CH$_2$—), ethyleneoxyacetimidoyl, ethyleneoxyethylenethiocarbamoyl, propyleneoxypropylenecarbamoyl, and diethyleneoxyacetimidoyl.

Turning now to a consideration of individual compounds, the first group of compounds are the alkaloids. Of particular interest among the alkaloids are the opiate alkaloids which will have for the most part the following formula:

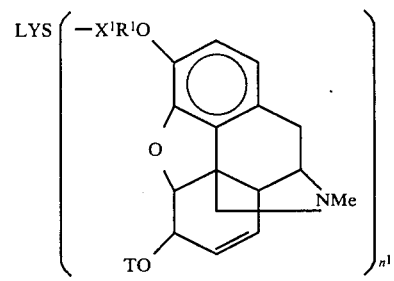

wherein:

T is hydrogen or acetyl, usually hydrogen;

$n^1$ is on the average 1 to 5, usually 2 to 4;

$R^1$ may be the same as R, but will usually be either (1) an aliphatic group, either branched or straight chain, having from 0 to 1 site of aliphatic unsaturation, e.g. ethylenic and of from 1 to 8 carbon atoms, more usually of from 1 to 6 carbon atoms, and preferably of from 1 to 4 carbon atoms, and has from 0 to 3, usually 0 to 2 heteroatoms, which are oxygen, sulfur or nitrogen, usually oxygen and nitrogen, and bonded to X with other than sulfur and oxygen, and bonded to oxygen through carbon, wherein the oxygen is present as oxocarbonyl or oxy, particularly ether, and the nitrogen is present as tertiary amino; or (2) aromatic hydrocarbon, e.g. arylene, alkarylene or aralkylene of from 6 to 9 carbon atoms; and $X^1$ is a bond, non-oxo-carbonyl (including thio and imino analogs thereof), or diazo, when bonded to an aromatic annular carbon atom, i.e. when $R^1$ is aromatic hydrocarbon.

Illustrative groups for —R$^1$—X$^1$— include carboxymethyl, imidoylmethyl, thiocarbamoylethyl, diazophenyl, ethylene, ethyleneoxyethylene, carboxymethyleneoxyethyl, 2-(1-carboxypropylene) and N-methyl imidoylmethylaminoethyl.

The next group of compounds are cyclic lactams, including urea derivatives, which are found in such drugs as barbiturates, diphenylhydantoin, primidone, glutethimide and zerontin. For the most part, the lysozyme conjugates will have the following formula:

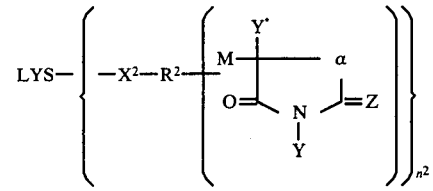

wherein:

$X^2$ is a bond or non-oxo-carbonyl (including thio and imino analogs thereof;

$R^2$ is a linking group of from 1 to 12 carbon atoms, usually 1 to 6 carbon atoms, and 0 to 2, usually 0 to 1 heteroatoms in the chain, chalcogen or nitrogen (tertiary amino) and may be aliphatic, alicyclic, aromatic or heterocyclic, either aliphatically saturated or unsaturated, usually 0 to 1 site of ethylenic unsaturation;

M is hydrocarbyl of from 1 to 8 carbon atoms, more usually of from 1 to 6 carbon atoms, and may be aliphatically saturated or unsaturated, usually having from 0 to 1 site of ethylenic unsaturation (hydrocarbyl intends an organic radical composed solely of carbon and hydrogen, which may be aliphatic, alicyclic, aromatic or combinations, thereof, which may be aliphatically saturated or unsaturated, usually having not more than two sites of ethylenic unsaturation, more usually having not more than one site of ethylenic unsaturation), more particularly M will be phenyl or alkyl of from 1 to 6 carbon atoms, more usually of from 2 to 6 carbon atoms;

Z is $H_2$ or oxygen;

$\alpha$ is imino, methylene, ethylene, or carbamoyl, being carbamoyl when Z is $H_2$;

one of Y and Y° is a bond, when other than a bond, Y is hydrogen or lower alkyl of from 1 to 2 carbon atoms, usually hydrogen or methyl; and Y° is hydrocarbyl of from 1 to 8 carbon atoms, more usually of from 1 to 6 carbon atoms, having from 0 to 1 site of ethylenic unsaturation, generally aliphatically saturated, and is particularly phenyl or alkyl of from 1 to 6 carbon atoms, or allyl, more particularly Y° is phenyl when $\alpha$ is imino, lower alkyl of from 1 to 3 carbon atoms when $\alpha$ is methylene or ethylene, and alkyl of from 2 to 6 carbon atoms or allyl when $\alpha$ is carbamoyl;

$n^2$ is 1 to 5, more usually 1 to 4, and preferably 2 to 4.

Where the drug of interest is a diphenylhydantoin, the lysozyme conjugate will have the following formula:

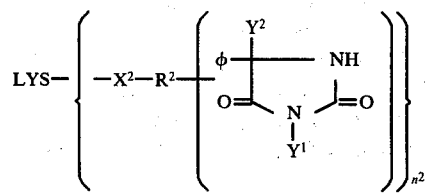

wherein:
where with the exception of $Y^1$ and $Y^2$, the symbols have been defined previously;
one of $Y^1$ and $Y^2$ is a bond, but when other than a bond $Y^2$ is phenyl and $Y^1$ is hydrogen;
when $Y^2$ is the bond, $R^2$ is preferably aromatic, particularly phenoxyalkyl of from 7 to 8 carbon atoms (with an annular carbon atom bonded to the hydantoin ring), and when $Y^1$ is the bond, $R^2$ is preferably aliphatic and particularly preferred saturated aliphatic of from 1 to 3 carbon atoms.

When the drug of interest is ethosuximide, for the most part, the conjugate will have the following formula:

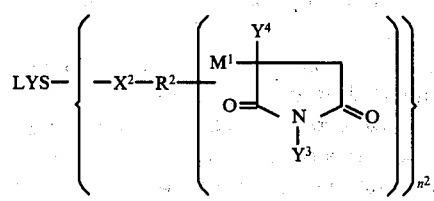

wherein:
the symbols have been defined previously, except for $M^1$, $Y^3$ and $Y^4$, with $M^1$ being methyl or ethyl; one of $Y^3$ and $Y^4$ being a bond when other than a bond, $Y^4$ is the other of methyl and ethyl and $Y^3$ is hydrogen; preferably, $R^2$ will be aliphatic, preferably saturated aliphatic.

When the drug is a barbituric acid or 2-desoxo barbituric acid, the conjugate will for the most part have the following formula:

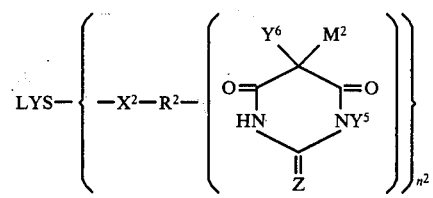

wherein:
the symbols have been defined previously, except $Y^5$, $Y^6$ and $M^2$; wherein one of $Y^5$ and $Y^6$ is a bond, when other than a bond, $Y^5$ is hydrogen or methyl, and $Y^6$ is hydrocarbyl of from 1 to 8 carbon atoms, particularly of from 1 to 6 carbon atoms, and more particularly of from 2 to 6 carbon atoms, having from 0 to 1 site of ethylenic unsaturation, e.g. ethyl, 2-butyl, 2-pentol, cyclohexyl, phenyl, allyl, etc.;

$M^2$ is hydrocarbyl of from 1 to 8 carbon atoms, usually of from 2 to 6 carbon atoms, having from 0 to 1 site of ethylenic unsaturation and may be the same or different from $Y^6$, usually being different, generally being aliphatic when $Y^6$ is aromatic, and is particularly phenyl or ethyl when Z is $H_2$;

$R^2$ is preferably aliphatic, particularly preferred aliphatic having from 0 to 1 site of ethylenic unsaturation.

When the drug of interest is methadone, the compounds for the most part will have the following formula:

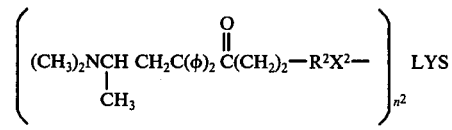

wherein:
all the symbols have been defined previously;
$R^2$ is preferably an aliphatic radical of from 1 to 8 carbon atoms, usually of from 1 to 6 carbon atoms, and more usually of from 1 to 4 carbon atoms, having from 0 to 3 heteroatoms, more usually 0 to 1 heteroatom, which are oxygen, sulfur and nitrogen, particularly heteroatoms of atomic number 7 to 8 and having from 0 to 1 site of ethylenic unsaturation, preferably saturated.

The next compounds are cocaine derivatives, particularly ecgonine derivatives which are metabolites of cocaine and will for the most part have the following formula:

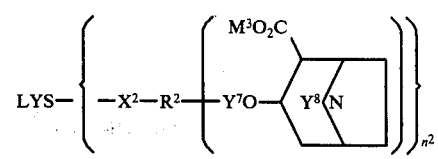

wherein:

all of the symbols have been defined previously, except M³, Y⁷ and Y⁸;

M³ is hydrogen or methyl;

one of Y⁷ and Y⁸ is a bond, and when other than a bond, Y⁷ is hydrogen or benzoyl and Y⁸ is methyl;

R² is preferably carbocyclic aryl, particularly phenyl, bonded to X² through amino to form a carbamoyl or thiocarbamoyl.

The next group of compounds are amphetamine derivatives, which for the most part have the following formula:

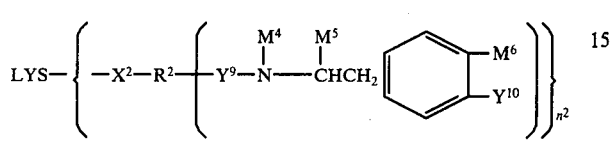

wherein:
all of the symbols have been defined previously, except M⁴⁻⁶ and Y⁹⁻¹⁰;

M⁴ is hydrogen or methyl;

M⁵ is hydrogen, methyl or carboxyl, preferably methyl;

M⁶ is hydrogen, hydroxyl or methoxyl, preferably hydrogen;

one of Y⁹ and Y¹⁰ is a bond, when other than a bond, Y⁹ is hydrogen and Y¹⁰ is hydrogen, hydroxyl or methoxyl, preferably hydrogen;

R² is preferably aliphatic hydrocarbon of from 1 to 5, more usually of from 1 to 4 carbon atoms, and having from 0 to 1 site of ethylenic unsaturation.

The next group of compounds are based on the drug meperidine and for the most part will have the following formula:

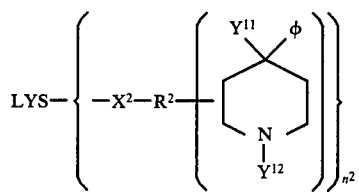

wherein:
all of the symbols have been defined previously, except Y¹¹ and Y¹²;

one of Y¹¹ and Y¹² is a bond, when other than a bond, Y¹¹ is carboalkoxy, particularly alkoxy of from 1 to 3 carbon atoms, more particularly 2 carbon atoms, and Y¹² is methyl;

R² is preferably a bond or alkyl group of from 1 to 3 carbon atoms when Y¹¹ is a bond.

The next group of compounds are based on the drug propoxyphene and will for the most part have the following formula:

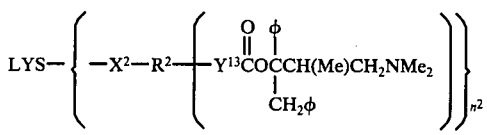

wherein:
all of the symbols have been defined previously, except Y¹³, and Y¹³ is a bond;

R² is preferably aliphatic, particularly saturated aliphatic of from 1 to 4, preferably 2 to 3 carbon atoms.

The next group of compounds are based on the benzdiazocycloheptanes, particularly those drugs related to oxazepam. The oxazepam related drugs will for the most part have the following formula:

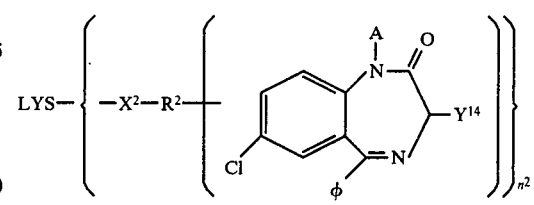

wherein:
all of the symbols have been defined previously, except A and Y¹⁴;

A is hydrogen or lower alkyl of from 1 to 3 carbon atoms, particularly methyl or hydrogen;

Y¹⁴ is a bond, oxy, or oxycarbonyl; and

R² is preferably aliphatic, particularly having from 0 to 1 site of ethylenic unsaturation, preferably saturated and of from 1 to 4 carbon atoms, more usually of from 1 to 3 carbon atoms.

The next group of compounds are related to tetrahydrocannabinol and its derivatives including those having different degrees of unsaturation. For the most part, these compounds will have the following formula:

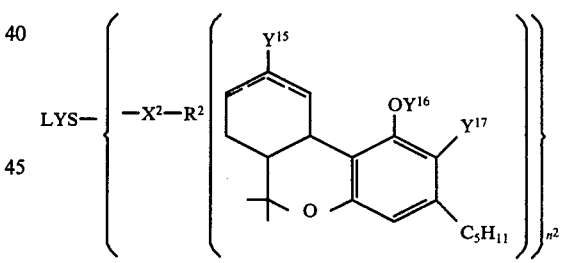

wherein:
all of the symbols have been defined previously, except Y¹⁵⁻¹⁷;

one of Y¹⁵ to Y¹⁷ is a bond, when other than a bond, Y¹⁵ is methyl, Y¹⁶ is hydrogen or methyl and Y¹⁷ is hydrogen;

when Y¹⁵ is a bond, R² is preferably a bond or an aliphatic hydrocarbon group of from 1 to 4 carbon atoms having from 0 to 1 site of ethylenic unsaturation and otherwise saturated; and when Y¹⁷ is a bond, R¹ is azophenyl and X² is carbonyl.

The broken line indicates the presence of a double bond at one of the positions.

The next group of compounds are based on the polyiodothyronines and these compounds will for the most part have the following formula:

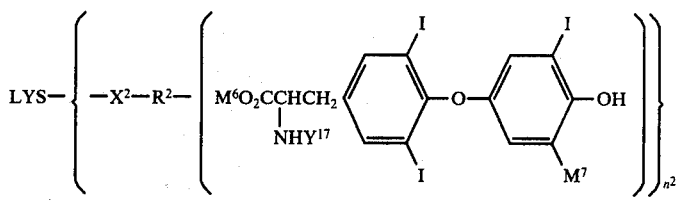

wherein:
all of the symbols have been defined previously, except $M^{6-7}$ and $Y^{17}$;
$M^6$ is hydrogen or lower alkyl of from 1 to 6 carbon atoms, usually methyl;
$M^7$ is hydrogen or iodo;
$Y^{17}$ is a bond;
$R^2$ will generally be aliphatic of from 1 to 6, more usually 1 to 4 carbon atoms, having from 0 to 1 site of ethylenic unsaturation, and from 1 to 2 heteroatoms in the chain of atomic number 7 to 8 with the heteroatoms bonded only to carbon and will be bonded to nitrogen through carbonyl.

Preparation of Conjugates

In preparing the conjugates, it is desirable that at least 20, preferably at least 40, and particularly preferred at least 50 percent of the original enzyme activity is retained. Furthermore, the enzyme is substituted in such a manner so that when one or more groups are bonded to the enzyme and are bound by antibody, the activity of the enzyme is reduced by at least 30 percent of its original activity after conjugation, usually at least 40 percent, and preferably by at least 50 percent.

Various ways can be employed for conjugating the various compounds or ligands to the lysozyme. The conditions employed will normally reflect the particular functionality which is employed in forming a bond to the lysozyme. The functionalities which find primary use are the mixed anhydride employing an alkyl chloroformate, acyl azide, the imidate ester, thioimidate ester, isothiocyanate, or an isocyanate. Normally, the groups will be bonded to available amino groups of lysine as the major mode of conjugation, and therefore amides, amidines, ureas and thioureas will be formed.

The reaction mixture will normally be buffered to a pH in the range of 5 to 10, more usually in the range of 6 to 9. Various buffers may be used such as phosphate, carbonate, Tris, and the like. An aqueous solvent will normally be used, and for difficult conjugations a preferred solvent includes from about 10 to 40 weight percent of an oxyethylene alcohol or ether having from 1 to 3 oxyethylene units. Particularly useful is carbitol. The temperatures will normally be at or above $-5°$ C, and generally less than about 40° C, usually from about 0° to 25° C.

The concentration of the enzyme will vary widely, generally ranging from about 0.05 to 20, and more usually from about 0.1 to 10mg/ml. The amount of ligand to be conjugated will vary depending on the ligand enzyme ratio which is desired.

EXPERIMENTAL

The following examples are offered by way of illustration and not by way of limitation. All percents not otherwise indicated are intended to be by weight. Pressures are normally reported in mm Hg.

EXAMPLE I

A first solution (solution A) was prepared by dissolving 100mg of lysozyme ($6.9 \times 10^{-6}$ mole) in 10ml of water and adding sodium carbonate until a pH of 8.0 was obtained.

A second solution was prepared by suspending 34.3mg ($1 \times 10^{-4}$ moles) of carboxymethylmorphine in 2ml of anhydrous DMF. After cooling to $-15°$ C, 13.1μl of isobutyl chloroformate ($1 \times 10^{-4}$ moles) was added to form a mixed anhydride. The solution was stirred at $-15°$ C for about 30 minutes at which time the solids had dissolved.

Solution A was cooled in an ice bath and the above morphine mixed anhydride added. After storing at 4° for 14 hours, the solution was dialyzed against distilled water for 4 days (2,000ml of water replaced twice daily).

The protein was lyophilized and the residue dissolved in 10ml of 0.128M sodium phosphate, pH 7.15. The product mixture was fractionated on a weak acid cation exchange resin coluum (Biorex 70), eluting at a rate of 1ml per minute with a 400ml linear gradient ranging from 0.128 to 0.400M sodium phosphate, pH 7.15. The eluent was collected in 2ml fractions. The chromatography was continuously monitored by measuring ultraviolet absorption at 280nm. Five fractions were obtained. The lysozyme activity was measured according to the following technique.

A 0.35mg/ml suspension of dried bacteria, Micrococcus lysodeikticus, in 0.05M sodium phosphate, pH 7.0 is prepared. To 2.85ml of the suspension contained in a 3ml cuvette is added 0.10ml of 8.76 percent (W/V) (g/l.) sodium chloride solution and 0.025ml enzyme solution ($7.5 \times 10^{-6}$g of protein). The contents are mixed and placed in a spectrophotometer set at 436nm at 30°. The rate of decrease of optical density with time is recorded and the rate expressed as optical density units per minute per $7.5 \times 10^{-6}$g of protein. The following table indicates the fractions, the milligrams of protein per milliliter, and the rate of reaction.

| Fractions | mg protein/ml | rate OD/min/ $7.5 \times 10^{-6}$g protein |
|---|---|---|
| a | 0.15 | 0.027 |
| b | 0.18 | 0.033 |
| c | 0.26 | 0.040 |
| d | 0.28 | 0.047 |
| e | 0.31 | 0.043 |
| Lysozyme | 0.30 | 0.070 |

Except where otherwise indicated, the following is the procedure for assaying when the ligand is conjugated to lysozyme. A buffer solution is prepared of Tris-maleate, 0.025M, pH 6.0, by dissolving 3.03g of Tris and 2.9g of maleic acid in 800ml of distilled water. After adjusting the pH to 6 with 1N sodium hydroxide, the solution is diluted to a final volume of 1 liter. A 0.1 weight percent bovine serum albumin (BSA) solution in the above buffer was prepared by diluting 1g of BSA in 1 liter of the buffer. A substrate solution was prepared by suspending 30mg of M. lysodeikticus (also referred to as M. luteus) (Miles, lyophilized) in 50ml of the above buffer, prepared 12 hours before use and stored at 4° in a plastic container. The stock solution of the carboxymethylmorphine conjugated to lysozyme is diluted with the BSA solution so as to obtain a reagent solution having a rate of lysis of about $0.210 \pm 0.020$ OD/min.

The active lysozyme content of the working solution is determined by measuring at 436nm the rate of bacterial lysis at 30°. The solution is prepared by mixing 0.200ml of bacterial solution, 0.020ml of the BSA solution, 0.080ml of synthetic urine, and 0.500ml of the enzyme solution.

The antibody solution employs a 0.025M Tris-Maleate buffer at pH 7.4 and is employed in a sufficient amount in the assay to inhibit 92–96 percent of the enzyme activity of the stock enzyme solution.

In carrying out the assay 0.2ml of the bacterial suspension is pipetted into a flask to which is added 20μl of the antibody solution. A urine sample is then introduced carefully, and 0.5ml of the enzyme solution added. The reaction mixture is then aspirated into the spectrometer and the decrease in optical density measured at 436nm for 10 seconds (any time interval from 10–60 seconds may be used) at 30°. The concentration of morphine present in the urine sample may then be determined from a standard curve.

EXAMPLE 2

A. To a solution of 5g of morphine monohydrate in 40ml of dry dimethyl formamide (DMF) and 300ml of acetone, 25g of finely powdered potassium carbonate and 5ml of chloroacetonitrile was added. The solution was allowed to reflux for 20 hours, cooled to room temperature and filtered. The filtrate was washed three times with acetone-DMF in a 20:1 mixture and then evaporated to dryness in vacuo. Methylene chloride (500ml) was added and the mixture heated to reflux, filtered while hot and the filtrate evaporated to give a brown oil. Addition of 200ml of ethyl acetate led to crystallization by cooling overnight in the icebox. Total yield, 4.4g of cyanomethylmorphine. m.p. 186°–188°.

B. To a solution of 1.0g (3.09 mmoles) of cyanomethylmorphine in 50ml of dry methanol was added 7ml of a 0.0435M sodium methoxide solution in methanol. The reaction was allowed to stir at room temperature for 48 hours. After this time 18μl of glacial acetic acid was added, the reaction mixture was stirred and then evaporated to dryness. The residue was dissolved with ethylene chloride and filtered to remove sodium acetate. After filtration, the organic phase was evaporated to give 1.2g of a light yellow salt.

C. A solution of 18mg (0.5mg) of $O^3$-methoxyimidoylmethylmorphine in 0.5ml of dry DMF was added dropwise to a cold (0°) solution of 60mg of lysozyme in 6ml of water. The aqueous solution was first adjusted to pH 7.5 with 0.05M sodium hydroxide. The solution was then stirred at 0° overnight. The pH was adjusted to 7 and the aqueous solution was dialyzed against water for 48 hours. The resulting dialysate was suitable for enzyme immunoassay. It could be inhibited by morphine antibodies, and full recovery of activity could be achieved upon the addition of an aqueous solution of morphine.

EXAMPLE 3

A. A solution of tetramethylene dibromide (32.4g, 150 mmoles) in dry ether (150ml) was added to magnesium (10.9g, 450 mmoles) in ether (80ml) at such a rate that the ether refluxed. The reaction was carried out under argon. After the addition was completed, the reaction mixture was boiled for one hour. A solution of 2,2-diphenyl-4-dimethylaminovaleronitrile (I), (prepared according to J. W. CUSIC, J. Am. Chem. Soc., 71, 3546, (1949)) (8.4g, 30 mmoles) in dry xylene (100ml) was added during 30 minutes at room temperature, and the mixture was stirred at 55° for 1 hour. The reaction mixture was cooled in an ice-water bath and $CO_2$ was passed through with fast stirring for 4 hours. Water (200ml) and concentrated HCl (100ml) were added, the magnesium filtered off, and the filtrate refluxed for 2 hours. The cooled clear solution was washed with ether (3 × 150ml) and extracted with dichloromethane (3 × 150ml). This extract was evaporated to dryness, and the residue dissolved in 0.5 liter of 0.5N sodium hydroxide.

This solution was washed with ether (3 × 100ml), made acidic with conc. HCl (150ml), saturated with sodium chloride and extracted with dichloromethane (3 × 200ml). Evaporation of the solvent left an oil (7.55g, 60%) 6-keto-7,7-diphenyl-9-(dimethylamino)decanoic acid hydrochloride, which moves as a single spot on TLC ($HCCL_3$:MeOH 8:2 and 7:3).

| U. V. Spectrum | |
|---|---|
| 0.02% $CF_3COOH$ | |
| | 293 ($\epsilon$ = 540); |
| | 264 ($\epsilon$ = 500); |
| λmax | 259 ($\epsilon$ = 535); |

B. The acid, 20.1mg (50μmoles) was dissolved in 1ml dry dimethylformamide, 2 drops of triethylamine were added, and the chilled solution was treated with 6.5μl of isobutylchloroformate as described previously in other preparations.

C. Lysozyme (120mg, 50μmoles of lysine) was dissolved in 12ml of water. The pH was adjusted to 10 with 0.05N sodium hydroxide, and maintained there during the dropwise addition of the mixed anhydride solution. After 30 minutes additional stirring the mixture was centrifuged. The supernatant fraction remained homogeneous through dialysis against water and contained the lysozyme conjugate to the methadone analog.

D. The assay employed is described in Example 1 for the carboxymethylmorphine lysozyme conjugate. The compositions employed were an enzyme solution at a concentration of $1.6 \times 10^{-5}M$ and an antibody solution having a concentration of $3.66 \times 10^{-5}M$ based on binding sites, and having a binding constant of $6.55 \times 10^7$. The reagent solutions were combined to have an enzyme concentration at $2 \times 10^{-7}M$, an antibody concentration based on binding sites of $2.3 \times 10^{-7}M$ and a total volume including 0.080ml of urine of 0.800ml. Readings were taken at 40 seconds. Sensitivity to methadone was found to be $1 \times 10^{-6}$ (0.35μg/ml).

EXAMPLE 4

A. 4-Cyano-4-phenylpiperidine hydrochloride (2.23g) was dissolved in 15ml water to which was added 4ml of 50 percent aqueous potassium hydroxide. The oil was extracted with 3 × 15ml ether and the organic layers were dried over an anhydrous magnesium sulfate. Filtration and evaporation of the solution gave a residue which was placed in a glass ampoule along with 3ml of methanol and 1.23ml of 50 percent aqueous potassium hydroxide. The sealed ampoule was heated to 165°–170° for 3.5 hours and diluted with 50ml water. After extraction with chloroform the aqueous phase was neutralized with DOWEX 50-X8 (H+form) to pH 6. Filtration and evaporation yielded a residue (0.82g) which melted above 300°. Recrystallization from water and drying over phosphorous pentoxide gave a compound with m.p. 285°–286°.

B. 4-Carboxy-4-phenypiperidine (1.8g) was refluxed in 50ml of 5 percent ethanolic hydrochloride for four hours. The residue on evaporation of the solvent was dissolved in acetone and the insoluble part filtered off. From the acetone solution a viscous oil remained on evaporation which crystallized on standing; m.p. 107°–110° (1.068g). It was used without further purification.

B'. A solution of about 7.2g of 4-cyano-4-phenylpiperidine hydrochloride in 6ml 66 percent sulfuric acid was heated to 45° and stirried for 45 minutes. On cooling to 125° the solution became slightly more viscous. The addition of alcohol (stem of the addition funnel below the surface of the reaction mixture) lowered the temperature to 105°. It was kept there for 4 hours. During the first hour 20ml alcohol were added, in the next hours 6ml each. The alcohol vapors were removed by a continuous distillation. At the end of the addition the temperature was raised to 125° until condensate is no longer formed. The hot solution was poured into 6ml water/40g ice containing 8g sodium hydroxide. After extraction with ether 3 × 70ml, drying over anhydrous magnesium sulfate and removal of the solvent, an oil remained which was distilled at 112°–115°/0.2 mm Hg, 4.01g (54%).

C. 4-Carbethoxy-4-phenylpiperidine (4.01g) was dissolved in 13ml absolute alcohol and refluxed together with 2.01g sodium chloroacetate. After 7 hours, no starting material was present as evidenced by TLC. The precipitated sodium chloride was removed by filtration and washed with 3ml ethanol. On cooling of the filtrate white crystals appeared. Filtration and drying gave 2.9g (58%) of the title compound. m.p. 138°–140° C. Evaporation of the mother liquor gave a glass which did not crystallize from acetone/hexane.

D. To a solution of 29.7mg. (0.1 mmole) of 4-carbethoxy-1-carboxymethyl-4-phenylpiperidine in 1.0ml dry dimethyl formamide at 0° was added 13.1µl isobutyl chloroformate (0.1 mmole). The mixture was stirred at 0° for 1 hour.

E. The cold solution of mixed anhydride (prepared above) was added dropwise to a solution of 100mg lysozyme 6.9µmole) and 100mg sodium bicarbonate in 10ml water at 0°. The reaction was stirred at 4° for 24 hours then dialyzed against water for 48 hours. The water was changed three times a day. The partially purified enzyme conjugate was then chromatographed on Bio-Rex-70 using a 0.05–0.20M pH 7.15 phosphate buffer gradient. Lysozyme activity in the eluent was followed by the conventional lysozyme assay employing Micrococcus lysodeikticus (20mg/50ml buffer). The addition of γ-globulin from rabbit or sheep immunized with the BSA-conjugate of the meperidine acid caused the lysozyme-meperidine conjugate to be nearly completely inhibited. Addition of free meperidine to the inhibited enzyme-antibody complex led to restoration of lysozyme activity.

EXAMPLE 5

A. Amphetamine sulphate (3.68g, 20 mmoles of amine) was dissolved in 0.5N sodium hydroxide (80ml). The alkaline solution was extracted with ether, the ether dried and evaporated. The residue was dissolved in benzene (50ml) and diisopropylethylamine (3ml) was added followed by ethylbromoacetate (2.2ml, 20 mmoles). The reaction mixture was refluxed for one hour, cooled, filtered and the filtrate evaporated. The residue was taken up in ether, washed several times with water, the ether dried and evaporated. The pure amino-ester was obtained by column chromatography on silica (hexane:ether 7.3). Yield 3.1g (70%), NMR and IR agree with the structure.

B. The amino-ester (2.5g, 11.3 mmoles) was dissolved in 1:1 mixture of methanol and 1N sodium hydroxide (50ml) and left at room temperature overnight. The mixture was evaporated to a small volume, washed twice with ether (2 × 25ml) and acidified to pH 6 with conc. HCl. The crystals that separated out were recrystallized from ether-acetone to give two fractions: 900mg, m.p. 222°–25° (m.p. lit. 220°–5° C, Tetra. Letters. 1966, 4603-7) and 450mg, m.p. 219°–218°. Only the first fraction was used for further reactions. $\lambda_{max}^{H_2O}$ 257nm, $\epsilon=159$.

C. N-carboxymethyl amphetamine (25mg, 0.133 mmole) was suspended in 1.8ml of dry dioxane at 40° C. Phosgene (12.5 volume percent in benzene) (0.715ml) was added in one portion. The reaction mixture was stirred at 40° for 3½ hours before an additional 0.2ml of phosgene (12.5 volume percent in benzene) was added. After stirring an additional 30 minutes the solution became homogeneous. The solvent was removed in vacuo at 25° in the hood. An additional 0.70ml of dry dioxane was added for use in the next step.

D. The cold dioxane solution of the above product was added dropwise over 5 minutes to a stirred, cold (0°) solution of 200mg sodium bicarbonate and 100mg lysozyme in 10ml water. The milky reaction mixture was stirred at 4° for 48 hours, and then dialyzed against water (1 liter changed three times daily) for 48 hours. The residue was lyophilized and the residue used for activity and inhibition studies.

EXAMPLE 6

A. Sodium phenobarbital (5.08g, 0.02 moles), methyl chloracetate, (2.16g, 0.02 moles) methanol (14ml) and a catalytic amount of DMF (1ml) were refluxed for 2 hours. A white precipitate separated out during this period. The reaction mixture was cooled to room temperature and filtered. The methanolic filtrate was evaporated to dryness to yield about 5g of a gummy material which solidified on standing. (The precipitate from the above filtration partially dissolved when rewashed with distilled water. The water-insoluble material, about 50mg, proved to be the dialkylated product.)

The solidified material was stirred with 20ml of 1N NaOH solution for 15 minutes and then filtered. This separated the alkali-insoluble derivatives, the monoalkylated product and unreacted phenobarbital. The alkaline filtrate was acidifed with conc. HCl to a pH 2 and the white gummy precipitate which was taken up in methylene chloride.

Drying (MgSO₄) and evaporation of the organic solvent yielded 4g of gummy material. This was dissolved in benzene and chromatographed over a column of silica gel (40g). Elution was with chloroform and 100ml fractions were collected. (The progress of the chromatography was followed by TLC, since the dialkylated product has an $R_f$ 0.1 with chloroform/methanol 95:5.)

Fractions 2–5 combined yielded on evaporation 1.6g of a gum which solidified on standing. Trituration with petroleum ether and filtration yielded 1.5g of a white powder which was shown by NMR to be the required monoalkylated derivative, N-methoxycarbonylmethyl phenobarbital.

Further elution with chloroform (500ml) yielded 1.5g of a white solid which was shown to be unreacted phenobarbital.

B. The monoester prepared above (1g) was refluxed with 10ml of 20 percent HCl solution for 3.5 hours. The cooled reaction mixture was diluted with water (20ml) and extracted with ether. Evaporation of the other extract yielded 0.98g of a colorless gum which very slowly solidified on standing. NMR and TLC showed that complete hydrolysis had occurred to the acid.

A pure sample of the acid was prepared by preparative TLC for UV analysis, with chloroform/methanol (5:1) as eluent.

C. To a cold (0°) solution of 29.6mg N-carboxymethyl phenobarbital (0.1 mmoles) and 14.3µl triethyl amine (0.1 mmoles) in 1.0ml dry dimethyl formamide was added 13.1µl isobutyl chloroformate (0.1 mmoles). The solution was stirred at 4° for 1 hour before use.

D. The cold solution of mixed anhydride was added dropwise with stirring to a cold (4°) solution of 0.100g lysozyme (6.9 mmole) and 0.100g sodium bicarbonate in 10ml water. The resulting heterogeneous solution was stored at 4° for 48 hours before being dialyzed against water for 48 hours. (The water was changed three times daily.) The dialysate was then chromotographed on Bio-Rex 70 employing a 0.05–0.20M pH 7.15 phosphate buffer gradient for elution.

E. The assay employing the phenobarbital conjugate had an enzyme concentration in the enzyme conjugate stock solution of $1.71 \times 10^{-5}$M, an antibody concentration based on binding sites in the stock solution of $1.66 \times 10^{-5}$ and a binding constant for the antibody of $5.94 \times 10^7$. The assay solution had a total volume of 0.800ml, employed a urine volume of 0.080ml, had an enzyme concentration of $2.14 \times 10^{-7}$ and an antibody concentration based on binding sites of $2.08 \times 10^{-7}$. The assay was carried out for 40 seconds and the sensitivity was found to be 0.3µg/ml, the minimum detectable amount.

EXAMPLE 7

A. Ozone was passed through a cooled (dry ice/acetone) solution of sodium secobarbital (2.6g, 0.01 mole) in methanol (250ml). After ozonlysis was completed (positive KI test), nitrogen was passed through the reaction mixture to remove all traces of ozone, and then dimethyl sulfide (7ml) was added to the cold solution with a syringe and allowed to stand overnight at room temperature. After evaporation of the solvent, the residue was diluted with water (20ml), acidified with conc. HCl and extracted with chloroform (3 × 20ml). The chloroform extract was dried (MgSO$_4$) and evaporated to yield 2.4g of gummy colorless material. NMR showed the presence of an aldehyde group at 89.7 ppm.

B. A sample of pure aldehyde (0.24g, 1 mmole), malonic acid (0.21g, 2 mmoles), 20ml pyridine and 1ml piperidine were refluxed together for 6 hours. The solvent was removed on the flash evaporator and the residue dissolved in 10 percent sodium bicarbonate solution. The bicarbonate solution was washed with ether (3 × 20ml) and then acidified with conc. HCl. Extraction with ether (2 × 20ml) and then with chloroform (2 × 25ml) followed by drying (MgSO$_4$) and evaporation of the combined organic layers yielded 0.23g (80 percent yield) of a white solid shown by NMR to be the desired acid 5-(γ-crotonic acid)-5-(1'-methylbutyl) barbituric acid. Recrystallization from CHCl$_3$/CCl$_4$ yielded 0.16g of pure material.

C. To a solution of 5-(γ-crotonic acid)-5-(1'-methylbutyl) barbituric acid, (0.282g, 1 mmole) in DMF (3ml), cooled to $-15°$ (ice-salt bath), there was added triethylamine (0.28ml, 2 mmoles) and isobutylchloroformate (0.13ml, 1mmole). Stirring was continued at $-15°$ for 15 minutes and then at 0° for 30 minutes.

D. Lysozyme, 240mg (100 µmoles of lysine) was dissolved in 20ml of water and the solution chilled to 0° C. The solution was adjusted to pH 10.2 with 0.05N sodium hydroxide and the mixed anhydride (100 µmoles) in 1.5ml dry dimethyl formamide added dropwise while the solution was kept between pH 9.6–9.9 by addition of base as required. The pH was maintained at 9.6 for another 30 minutes, after which time the mixture was centrifuged.

The supernatant was dialyzed against 0.05 mole Tris-maleate, pH 8.0. The pellet formed by centrifugation dissolved in 20ml 8M urea, and was dialyzed as described above, yielding additional amounts of enzyme. The urea dialysis treatment was repeated until only 10mg of insoluble material remained.

E. An enzyme stock solution was prepared of the secobarbital conjugate to lysozyme having a concentration of enzyme of $2.08 \times 10^{-5}$M. The antibody stock solution was $1.42 \times 10^{-5}$M based on binding sites, and the antibody had a binding constant of $8.4 \times 10^7$ by FRAT ®. In the assay solution, the enzyme concentration was $1.56 \times 10^{-7}$M, the antibody concentration based on binding sites was $2.66 \times 10^{-7}$M, the total assay volume was 0.800ml, the urine volume 0.080ml, the time for the assay 40 seconds, and the sensitivity found to be 0.2µg/ml.

EXAMPLE 8

Sodium hydride (0.85g of a 50 percent oil paste, 18 mmoles) was added in small amounts to a stirred solution of glutethimide, (3.7g, 17 mmoles) in dry DMF (10ml). Stirring was continued for about 5 minutes, when gas evolution was no longer observed. Sodium chloroacetate (2.2g) was then added, and the reaction mixture was stirred with heating in an oil bath at 100° for 3 hours. After cooling, the reaction mixture was diluted with 50ml water, acidified with conc. HCl, and then poured into 200ml ether. The ether layer was separated and washed with water (2 × 50ml). The organic layer was dried (MgSO$_4$) and evaporated to yield 3.4g of a white solid. Recrystallization from carbon tetrachloride/methylene chloride yielded the analytical sample of the acid.

The N-carboxymethyl glutethimide can be conjugated to lysozyme as set forth in the conjugation for the barbitals. Antibodies can be prepared by conjugating the N-carboxymethyl glutethimide to bovine serum albumin (BSA) and injecting the conjugated BSA into animals to obtain the appropriate antibodies. The assay is carried out in the same manner as previously described for lysozyme.

EXAMPLE 9

A. To a suspended solution of sodium phenobarbital (1.0g, 3.93 mmoles) in dry dimethylformamide (12ml) was added ethyl-5-bromovalerate (920mg, 4.43 mmoles) with stirring, and the mixture was heated at 40° for 10 minutes to give a clear solution. The mixture was stirred at room temperature for 15 hours, and then potassium iodide (200mg) was added to complete the reaction. The reaction mixture was then chromatographed by TLC (silica gel, 5 percent methanol — 95 percent chloroform). Most of the solvent was evaporated under reduced pressure to leave an oil, which was dissolved in dichloromethane (50ml) and washed with water. The solution was shaken once with 2.5 weight percent sodium carbonate solution (25ml) to remove unchanged starting phenobarbital. The dichloromethane layer, after being washed with water and dried over anhydrous sodium sulfate, was evaporated to leave an oil (1.4g). This oil was separated into two fractions by preparative TLC, silica gel. The oil was developed with 5 percent methanol — 95 percent chloroform, and each fraction was collected by cutting and extracted with acetone. The product, after removal of the solvent, was dissolved in dichloromethane, washed with water, and dried over anhydrous sodium sulfate. One fraction ($R_f$ 0.7) gave a colorless oil (0.5g, 36 percent) which proved to be analytically pure monoalkylated compound by IR and PMR spectra, and microanalysis.

B. The ethyl ester prepared above (120mg, 0.333 mmole) was dissolved into a mixture of conc. hydrochloric acid (2.5ml) tetrahydrofuran (5ml) and water (1ml), and then kept at room temperature overnight. After evaporation of tetrahydrofuran under reduced pressure, the residue was diluted with saturated sodium chloride solution (10ml) and extracted with dichloromethane. The dichloromethane layer was extracted with saturated sodium bicarbonate solution, and the combined alkaline layers, after being carefully acidified with conc. hydrochloric acid in an ice bath, were extracted with dichloromethane. The dichloromethane solution was washed with water, dried over anhydrous sodium sulfate, and evaporated to dryness to give an oily residue (100mg, 93 percent), which crystallized on standing. Recrystallization from ether/n-hexane gave an analytical sample of the desired acid.

C. A sample of the above prepared acid was dried overnight under vacuum at 80° before use.

In a flask protected from moisture, 166mg of the acid was dissolved in 5cc of dry DMF 150$\mu$l of triethylamine added. The solution was cooled to −15° and then 65$\mu$l (0.5 mmole) of isobutyl chloroformate added. The mixture was stirred for one hour with the temperature maintained between −5° and 0°.

D. Lysozyme (1.2g, 0.5 mmole lysine) was dissolved in 80ml distilled water in a beaker equipped with a magnetic stirrer. The solution was cooled in an ice-water bath to 4° and the pH was adjusted to 9.5 with 0.5M NaOH. The anhydride reaction mixture prepared above was added dropwise with stirring. The pH was kept at 9.5-9.7 during this addition by the slow addition of 0.5M NaOH. The solution was stirred an additional 90 minutes at 4°.

The pH was then lowered to 8.5 by the addition of 1M HCl and the mixture centrifuged at 12,000 rpm for 20 minutes. The supernatant fraction (S) was dialyzed against 6 changes of 0.05M Tris buffer pH 8.0. The precipitate on being stirred briefly with 100ml 8M urea dissolved completely ($P_1$). Upon dialysis (as for S) a significant amount of material came out of solution. The precipitated material, separated by centrifugation, was redissolved in urea and redialyzed ($P_2$, $P_3$, $P_4$ fractions). The various fractions of soluble enzyme ($P_1$, $P_2$, $P_3$, $P_4$, etc.) were all tested for inhibition with phenobarbital antisera (equal amount of antisera was used with all fractions). The fractions $P_1$, $P_2$, $P_3$ and $P_4$ showed inhibitions of 77, 85, 86, and 92 percent respectively. A pool of $P_2$, $P_3$ and $P_4$ was prepared for use in the assay.

EXAMPLE 10

A sample of the secobarbital acid prepared as described in Example 7, was dried overnight under vacuum at 80° before use.

In a flask equipped with a magnetic stirrer and a drying tube was dissolved 140mg of the above acid in 5ml dry DMF. After the addition of 137$\mu$l dry triethylamine the mixture was cooled to −15° and 68.5$\mu$l of isobutyl chloroformate added. The reaction was stirred at −5° to 0° for one hour and then conjugated to lysozyme.

A solution of lysozyme (1.2g, 0.5 mmole lysine) in 80ml distilled water was cooled in an ice bath to 4° and the pH adjusted to 9.5 with 0.5M NaOH. The acid anhydride prepared above was added dropwise with stirring as the pH was maintained at 9.5-9.7 by the slow addition of 0.5M NaOH. The heterogeneous reaction mixture was allowed to stir an additional 90 minutes at 4° before the pH was lowered to 8.5 with 1M HCl. The mixture was centrifuged at 12,000 rpm for 20 minutes. The precipitate on being stirred with 100ml 8M urea dissolved completely, but a significant amount of material came out of solution during dialysis (6 changes with 0.05M tris at pH 8.0). The dialysate was centrifuged and the supernatant ($P_1$) retained. The pellet was again suspended in 8M urea and dialyzed, and in this manner, a number of soluble enzyme fractions ($P_2$, $P_3$ ... $P_n$) were obtained. The precipitate fractions were all tested for their ability to be inhibited with seconal antisera (the same amount of antisera was used for all fractions). Inhibition of activity of 75, 80, 91 and 93 percent was obtained for fractions $P_1$, $P_2$, $P_3$ and $P_4$ respectively. The $P_1$ fraction was not considered suitable for use in the assays, but fractions $P_2$, $P_3$ and $P_4$ were all combined and used as a pool.

EXAMPLE 11

A. Cocaine (5g) was refluxed in 25ml water for 6.5 hours. The remaining oil after evaporation of the solution was dissolved in 5ml hot water. On cooling long white crystals separated (2.87g). Another 543g were obtained from the mother liquor.

B. Benzoylecgonine (1g) was refluxed in 25ml 2N hydrochloric acid for 1 hour. After cooling, the solution was filtered and extracted with ether. The aqueous phase was neutralized with sodium bicarbonate to pH 5.8. On evaporation, a white residue remained which was refluxed with 40ml ethanol (95 percent), filtered and the solvent evaporated. The oily residue (580mg) crystallized on addition of 0.5ml ethanol (130mg). m.p. 195°-197° (decomp).

C. To a suspension of 22.7mg (0.1 mmole) ecgonine hydrochloride in 1.0ml dry dimethyl formamide at 0° was added 13.7$\mu$l isobutyl chloroformate (0.1 mmole). The mixture was stirred at 0° for 2 hours and then used for the conjugation.

D. To a cold (4°) solution of 100mg lysozyme (6.9μ mole) and 100mg sodium bicarbonate in 10ml water was added the dimethyl formamide suspension of the mixed anhydride. The homogeneous solution was stirred at 4° for 40 hours and then dialyzed against water (1 liter changed three times daily) for 4 days. The dialyzed material was then lyophilized to dryness.

EXAMPLE 12

A. Ecgonine hydrochloride (5.5g, 24.8 mmoles) was dissolved in 35ml of methanol (dried over 3-A Molecular sieves) and saturated with dry hydrogen chloride keeping the receiver cool by immersion in an ice bath. Upon saturation the receiver was heated to 40° for 0.5 hour and evaporated to dryness in vacuo. The white residue was stored at 0.05mm Hg over potassium hydroxide for 16 hours and then dissolved in the minimum amount of hot methanol to which 200ml of boiling acetone was quickly added. After cooling in ice and filtering, there was obtained 4.2g of white crystals, m.p. 214°–215° (lit. 214°–215°). Evaporation of the mother liquor and repetition of the recrystallization yielded 0.8g, m.p. 212°–214°. Total yield was 86.3% of theory.

B. To 20ml of cold saturated potassium carbonate solution in a 125ml separator funnel was added a solution of 5.0g (213 mmoles) ecgonine methyl ester hydrochloride in 5ml water. The aqueous mixture was extracted with 4 × 60ml of chloroform. The combined chloroform extracts were dried over anhydrous sodium carbonate and evaporated in vacuo. Pumping at 0.05mm Hg for 15 minutes yielded 4.0g (93%) of TLC pure (20:1 CHCl$_3$:MeOH) ecgonine methyl ester.

The 4.0g (20:1 mmoles) ecgonine methyl ester was dissolved in 50ml dry benzene and then 30ml benzene was distilled off. To the cooled distillation pot was added 3.65ml triethylamine and a solution of 3.72g freshly recrystallized p-nitrobenzoyl chloride in 5ml of dry benzene was added dropwise with cooling (ice bath) and agitation.

The resulting sludge was stirred at 40° for 1 hour under nitrogen. After cooling to room temperature the reaction mixture was taken up in 100ml of chloroform and washed with 3 × 20ml 5 percent aqueous sodium carbonate solution. The chloroform solution was dried over sodium carbonate, evaporated in vacuo and pumped (0.05mm Hg) on overnight to yield 5.7g (85.3%) of yellow oil [one spot on TLC (95/5, CHCl$_3$/MeOH)] with same R$_f$ as known sample but having a slight odor of triethylamine. No further attempt at purification was made, and the product was used directly in the next step.

C. To a solution of 6.5g p-nitrococaine in 250ml absolute methanol was added 600mg 10% Pd/C under an N$_2$ blanket. The resulting mixture was hydrogenated at atmospheric pressure with rapid stirring and slight heating from the magnetic stirrer. After 0.5 hour, H$_2$ uptake ceased, [1.530 liters, calculated is 1.440 liters without correction for atmospheric pressure]. The catalyst was removed by suction filtration over a Celite pad in a fritted glass funnel (medium grade). The resulting clear solution was evaporated in vacuo to approximately 75ml and heated to dissolve crystals which formed and then allowed to cool to room temperature, followed by cooling in ice and filtering to give 4.0g white crystals, m.p. 188°–189°. The mother liquor was concentrated to 3ml, cooled in ice and filtered. After washing the crystals with 6ml of cold methanol, there was obtained 1.2g powdery crystals, m.p. 185°–188°. Total yield 88%.

D. p-Aminococaine (2.08g) in 15ml of water was refluxed with rapid stirring under nitrogen for 6 hours. The solution was allowed to cool to room temperature and then cooled in ice and filtered. The crystals were washed with 5ml cold water and dried at 0.05mm Hg for two hours to yield 1.2g clear needlelike crystals, m.p. 287° (dec). The compound slowly turns brown upon exposure to air and light. Recrystallization of 200mg from 2ml boiling water gave an analytically pure sample.

Calcd. %: C, 63.14; H, 6.62; N, 9.20; Found %: C, 63.32; H, 6.62; N, 9.16.

E. Into 2ml of 2N HCl under nitrogen was introduced 100mg (0.33 mmole) of para-aminobenzoyl ecgonine. To the solution was added 31μl (46mg) of thiophosgene and the heterogeneous mixture stirred vigorously under nitrogen at room temperature. After 10 minutes, the thiophosgene could no longer be observed. The product crystallized. The mixture was cooled in ice, filtered, and the filtrate washed with water. After drying the solid over phosphorous pentoxide and potassium hydroxide, 62mg was isolated. m.p. 257° (dec).

To the mother liquor was added approximately 3ml of the water, the solution cooled in ice and the precipitate collected. The second crop yielded 66mg. m.p. 257°.

F. A solution of 60mg (25μmole) lysozyme in 5.0ml water was cooled to 4° and adjusted to pH 9.0 with 0.05M NaOH. A total of 99.5mg (25μmole) p-isothiocyanatobenzoyl ecgonine was added in one portion to the alkaline protein solution. This conjugation was run on the pH-STAT at 4° with the machine maintaining the pH at 9.0 with 0.05M NaOH. (The reaction can also be performed by the manual addition of base using a pH meter to follow the course of the reaction.) After 3¾hours, the clear solution was adjusted to pH 9.5. Since no precipitation occurred, the pH was lowered to 7.0 with dilute HCl. The clear solution was dialyzed against water for 48 hours. The dialysate was immediately suitable for the assay of benzoyl ecgonine.

EXAMPLE 13

A. Ozazepam (2g, 7mmole) and succinic anhydride (1.2g, 11.2mmole) in pyridine (40ml, dried over barium oxide) were heated under a nitrogen atmosphere at 95° for 7 hours. The mixture was cooled, and the pyridine removed at reduced pressure. The residue was taken up in ethyl acetate and extracted into aqueous potassium carbonate, pH 13. After neutralizing the basic extracts with aqueous acid, the hemi-succinate was extracted into ethyl acetate, and the extracts washed with saturated brine. They were then dried, filtered, and concentrated in vacuo to give 2.1g (78%) of the crystalline hemi-succinate, which was recrystallized from ethyl acetate-cyclohexane: m.p. 204°–206° (lit. 204.5–205.5).

B. Into a reaction flask was introduced 20.4mg (5.04 × 10$^{-2}$ mmoles) of oxazepam hemi-succinate, 1 ml dimethylformamide and 15μl of triethylamine, and the mixture cooled to −15°. Isobutyl chloroformate (6.94μl, 5.3 × 10$^{-2}$ mmoles) is added, the mixture stirred for 45 minutes, while the temperature is allowed to rise to −5°.

This mixture is then added to a solution of 120mg (0.84 × 10$^{-2}$ mmoles) of lysozyme in 10ml water, pH 8.7, at 4°, the pH being adjusted with 0.05N sodium hydroxide. During the addition the pH is maintained at 8.7 and the reaction allowed to continue until the pH is constant for about 30 minutes. The pH is then adjusted to 7.0, the product centrifuged and dialyzed against pH 6.0, 0.025M Tris-maleate buffer.

EXAMPLE 14

A. Methyl succinate (20.5g) was heated with 20ml thionyl chloride to 40° for 3.5 hours. Excess thionyl chloride was removed by vacuum distillation (13mm Hg). The acid chloride (20.6g) was distilled at 43°-44°/0.2mm Hg.

B. 1,2-Diphenyl-3-methyl-4-(dimethylamino)butanol-2 hydrochloride (10g) was dissolved in water (~200ml) and extracted with chloroform (2 × 30ml yellow organic phase) to remove some insoluble compound. Addition of 2M potassium hydroxide to the aqueous phase gave a precipitate which was extracted with 2 × 10ml chloroform. The combined organic layers were dried over anhydrous magnesium sulfate. After filtration and evaporation of the solvent in vacuo (1 hour, 0.05mm Hg), an oil remained. It was dissolved in 150ml anhydrous toluene and heated to 100° together with 20g methyl succinate mono-acid chloride for two hours with exclusion of moisture. A precipitate formed immediately upon mixing which did not increase during the reaction. After standing overnight the precipitate was removed by filtration and centrifugation (1.2g) and the solvent was evaporated. The residue was dissolved in water and extracted with 2 × 100ml chloroform/2M potassium hydroxide. The combined organic layers gave a brown oil upon evaporation of the solvent. The oil was dissolved in anhydrous ether and hydrogen chloride passed through the solution. At first a precipitate occurred which later turned into an oil. The ether was decanted and the oily residue dissolved in 70ml warm benzene. Standing for two hours gave colorless crystals which increased on scratching the flask. The crystals (8.5g) were collected and dried in vacuo (m.p. 82°-88°, gas evolution). Upon slow evaporation of the ether, more colorless crystals were obtained.

For analysis the compound was recrystallized by dissolving in hot benzene and adding carbon tetrachloride.

C. The ester of Example B (8.5g) was dissolved in 20ml water and 6g of potassium carbonate in 30ml water added. A white precipitate appeared which was extracted with chloroform (2 × 50ml). The combined organic layers were dried over anhydrous magnesium sulfate, filtered and evaporated. The purity of the ester was evidenced by a single spot in the thin layer chromatogram (ether). The solvent was evaporated and the residue dried in vacuo yielding 7g of an oil. The oil was dissolved in a solution of 100ml methanol and 30ml water containing 6g of potassium carbonate. The mixture was refluxed for 30 minutes, cooled to room temperature and evaporated. A yellowish residue remained which was dissolved in water (50ml) and extracted with 5ml ether. The aqueous phase was diluted to 200ml and neutralized with BioRad 50W-X8 to pH 6.6. The resin had been previously washed until the washings were clear.

D. Into a reaction vessel was introduced 0.038g of the monoacid ester prepared above, 14$\mu$l of triethylamine, 14$\mu$l of isobutylchloroformate and 1ml of DMF. The mixture turned slightly cloudy and the reaction was allowed to continue until the mixture had turned yellow. The mixed anhydride thus prepared was then added dropwise to 120mg of lysozyme and 10ml water at pH 9.1. The mole ratio of the monoacid ester mixed anhydride to lysines of lysozyme was 2:1. A heavy white precipitate formed with the pH rising rapidly, and addition of 0.05N HCl was used to maintain the pH between 9-10. The reaction was continued for 4.5 hours and the pH was maintained by the addition of 0.05N sodium hydroxide in the range of 9.0-9.2. At the end of the reaction, the pH was adjusted to 7.0 with the precipitate dissolving and the solution dialyzed against 0.025M, pH 6.0 Tris-maleate buffer.

E. Into a reaction vessel was introduced 0.038g of the monoacid ester prepared previously, 14$\mu$l of isobutylchloroformate and 1ml of DMF. After sufficient time for completion of the formation of the mixed anhydride, the solution was then added dropwise to 120mg of lysozyme and 10ml of water at pH 9.1. The pH dropped and 0.05N sodium hydroxide was added to maintain the pH in the range of 9-10. The reaction was run for 2 hours at 4° at a pH of 9-9.5, and then adjusted to pH 8.5, with formation of a heavy white precipitate. The precipitate was removed by centrifugation, dissolved in 8M urea, and both the supernatant and the 8M urea solution dialyzed against 0.025M, pH 6.0 Tris-maleate buffer. The conjugated lysozyme in the two fractions was isolated.

EXAMPLE 15

A. Sodium nitrite (180mg) was added to a solution of p-aminobenzoic acid (500mg) in 20ml 1N HCl at 0° with agitation. The course of the reaction was followed with KI/starch paper and excess sodium nitrite destroyed with sulfamic acid. After stirring at 0° for 30 minutes, the solution was added dropwise with agitation to a methanolic solution of $\Delta^6$-tetrahydrocannabinol (1g/20ml). The pH was maintained at 10-11 during the reaction. After completion of the addition, the mixture was acidified to pH 1.5 with 0.1 1N HCl and extracted with chloroform (5 × 30ml). The combined organic extracts were washed with water, dried (MgSO$_4$) and evaporated to yield 0.9g of a dark red residue. Chromatography over silica gel was employed, removing unreacted THC with benzene-cyclohexane (4:1) followed by elution with chloroform yielding 0.4g of a crystalline material, which was recrystallized to produce two compounds: orange crystals, 100mg, m.p. 160°-164°; and violet crystals, 250mg, m.p. 102°-104°. The orange compound is the ortho derivative.

B. Into 0.5ml dry DMF was dissolved 23mg (50$\mu$ mole) of the above compound and 5$\mu$l triethylamine added. After cooling the solution to −15°, 7$\mu$l (50$\mu$mole) of isobutylchloroformate was added and the reaction mixture maintained at 0° for 45 minutes. To a solution of 50mg (21.25$\mu$mole lysines) of lysozyme in 5ml distilled water cooled in an ice-water bath and at a pH adjusted to 9.5 with 0.5M sodium hydroxide was added dropwise the above solution over a period of 10 minutes, while the pH was maintained at 9.5-10 by addition of 0.5N sodium hydroxide. The solution became milky and a red substance came out of the solution. Stirring was continued for 90 minutes while maintaining the temperature, at which time the pH was lowered to pH 8.5 by addition of 1M HCl and the mixture centrifuged at 20,000 rpm at 0.4° for 2 minutes in plastic tubes. The supernatant fraction (5.7ml) was dialyzed against 5 changes of 0.025M Tris-maleate pH 6.0 buffer (100ml each). A small amount of material precipitated. The supernatant fraction could be employed for an assay.

To obtain the desired rate of lysis, the supernatant was diluted 1:150.

EXAMPLE 16

A. A mixture of $\Delta^6$-THC (5g, 0.016 mole), methyl iodide (4.54g, 0.032 mole), anhydrous potassium carbonate (9g), and acetone (150ml) were stirred for 72 hours at room temperature, poured into water, and extracted 3× with ether. The ether extracts were combined, dried (MgSO$_4$) and evaporated to yield 4.8g of the methyl ether.

B. The crude $\Delta^6$-THC-methyl ether (2g), selenium dioxide (1.8g, 2.5 equiv.) and ethanol (100ml) were stirred under reflux for 24 hours, the mixture cooled, filtered and the filtrate evaporated to dryness. The residue was subjected to 200ml of water and the aqueous fraction extracted several times with ether. The combined ether extracts were dried (Na$_2$SO$_4$), evaporated to yield 1.9g which was chromatographed on a silica gel column (70g), eluting with 20 percent diethyl ether and petroleum ether to yield 0.35g of the aldehyde.

C. Into dry methanol (10ml) was introduced the above prepared aldehyde (0.23g, 0.67mmole), freshly prepared maganese dioxide (1.19g, 13.6mmole), sodium cyanide (0.17g, 3.5mmole) and approximately 0.15ml acetic acid, the mixture stirred at room temperature for 24 hours, filtered, and the filtrate evaporated to yield a residue which was mixed with water and extracted with ether. The combined ether extracts were dried (Na$_2$SO$_4$), and evaporated to yield 0.23g of the methyl ester as an oily residue.

D. The crude methyl ester was refluxed in 20ml of 5 percent methanolic sodium hydroxide for 2 hours, the reaction mixture concentrated on a flash evaporator to near dryness and then mixed with water, washed with ether several times, followed by acidification. The acidified aqueous layer was extracted 3× with ether, the ether dried (Na$_2$SO$_4$), the combined ether extracts evaporated yielding 0.18g of the desired acid.

F. Into 0.5ml dry DMF was dissolved 18mg (50µl) of the above acid and 5µl of triethylamine added. After cooling to −15°, 7µl (50µmole) of isobutylformate was added and the temperature maintained at 0° for 45 minutes.

Into 5ml of distilled water was dissolved 50mg (21.25µmole lysines) of lysozyme, the solution cooled in an ice-water bath, and the pH adjusted to 9.5 with 0.5M sodium hydroxide. The above prepared mixed anhydride was added dropwise during 10 minutes, while the pH was maintained at 9.5–10 by addition of 0.5M sodium hydroxide. The solution became milky and was allowed to stir for 90 minutes in an ice-water bath. After lowering the pH to 8.5 by addition of 1M HCl, the mixture was centrifuged at 20,000 rpm at 0.4° for 2 minutes in plastic tubes. The supernatant fraction (5.7ml) was dialyzed against 5 changes of 0.025M Tris-maleate pH 6.0 buffer (100ml each). A small amount of material precipitated and the supernatant was employed for the assay.

To obtain the desired amount of lysis, the supernatant was diluted 1:300. The percent inhibition using excess antibody prepared using a conjugate to the subject acid was 32.7 percent. Upon adding free acid, about 20 percent of lost activity was recovered.

EXAMPLE 17

A. To a solution of 1.65g of the methyl ester of thyroxine hydrochloride in 80ml of dry THF and 30ml of chloroform in a flask protected from light was injected 300µl of triethylamine while the mixture was agitated. Diglycolic anhydride (255mg, 2.2mmole) was then added, the mixture stirred overnight and the resulting solution washed 3× with water, dried over sodium sulfate, and the volatiles removed in vacuo. The residue was purified on a 30g Sephadex LH-20 Column using a solution of 20 percent methanol in dichloromethane as eluent. The clear fractions were collected, the solvent removed, and the residue precipitated from methanol with water, yielding 1.53g, 84 percent.

B. Into 5ml of dry DMF cooled in an ice-bath under nitrogen was dissolved 90.7mg of the thyroxine derivative, 11.5mg of N-hydroxy succinimide and 19.2mg of 1-ethyl-3-(3′-dimethylaminopropyl)carbodiimide hydrochloride (ECDI) and the mixture allowed to sit in the cold room overnight.

C. Into 2ml of water was dissolved 12mg of lysozyme and 0.84mg of sodium bicarbonate, the mixture cooled in an ice-bath and 2ml DMF added. To the mixture with stirring was added 0.5ml of the above thyroxine intermediate and 0.5ml of water. The mixture turned cloudy and after 3 hours the mixture was transferred to a dialysis bag and dialyzed against Tris-maleate, pH 6.0, 0.025M. A large precipitate was noted, the buffer was changed after 4 hours of dialysis and the dialysis continued overnight in the cold room. The dialysate was then centrifuged at 8,000 rpm for 15 minutes at 0°.

Upon testing the resulting product, it was found to be active, could be inhibited by thyroxine antibodies, and the activity returned by the addition of thyroxine.

Assays

The lysozyme conjugates of the subject invention are found to be useful in the determination of extremely small amounts of a wide variety of haptens. The antibodies which are employed will normally employ the same type of precursor, if not the same precursor, employed for the conjugation with lysozyme to be conjugated with an antigen such as bovine serum albumin, to prepare the antibodies.

In carrying out the assay, a number of reagent solutions are prepared:

A. Buffer solution: Tris-maleate, 0.825M, pH 6.0;

B. Bovine serum albumin solution: 0.1 weight percent BSA in Tris-maleate prepared above;

C. Bacteria: 40mg of M. luteus suspended in 50ml buffer solution. The suspension is prepared daily, 12 hours before use and stored at 4° C;

D. Hapten-lysozyme: the stock solution of hapten conjugated with lysozyme is diluted with 0.1 weight percent BSA and Tris-maleate and stored.

The active lysozyme content of the working solution is determined by measuring at 436nm the rate of bacteriolysis at 30°. The assay solution is prepared by mixing 0.2ml bacteria, 0.02ml, 0.1 weight percent BSA-buffer, 0.08ml synthetic urine (or urine where appropriate) and 0.50ml of the lysozyme solution. The antibody is employed in 0.025M Tris-maleate (pH 7.4) at a concentration suitable for 20µl to inhibit 92–96 percent of the hapten-lysozyme activity of the stock enzyme solution. The stock enzyme solution should provide about 0.15 milli OD units from a sample having no hapten to a sample where the hapten saturates the available antibody binding sites. (OD units are optical density units on a U.V. spectrometer at the measurement temperature.)

To prepare synthetic urine, 5.2g. potassium chloride, 8.2g sodium chloride, 1.4g sodium dihydrogenphosphate, 1.4g disodium monohydrogenphosphate, and 11g of urea are combined in one liter of distilled water.

In carrying out the assay, 20μl of the antibody solution is added to 0.2ml of the bacterial suspension. To this solution is added 80μl of urine and the mixture diluted with one-half ml of the enzyme solution. The mixture is then aspirated into the spectrometer and the decrease in optical density is measured at 435nm for 40 seconds. The concentration of hapten in the urine sample is read from a standard curve prepared by using standardized solutions and taking readings.

The first system to be considered is the morphine conjugate to lysozyme. Following the assay for lysozyme as previously described, cross-reactivities were carried out in order to determine which compounds other than morphine, the antibody would recognize, and would therefore provide a positive result for the assay. The following table illustrates the cross-reactivity for a number of compounds. The results show, that the antibody will recognize those compounds which have substantially the same ring structure as morphine, but would not recognize those compounds which do not have the same ring structure.

MORPHINE CROSS-REACTIVITY

| Compound | Concentration μg/ml | M | Percent max. rate |
|---|---|---|---|
| Codeine | 3 | $1 \times 10^{-5}$ | 90 |
|  | 0.3 | $1 \times 10^{-6}$ | 7 |
| Morphine glucuronide | 10 | $2.1 \times 10^{-5}$ | 77 |
|  | 0.3 | $6.35 \times 10^{-7}$ | 4 |
| Morphine | 3 | $1 \times 10^{-5}$ | 67 |
|  | 0.3 | $1 \times 10^{-6}$ | 5 |
| Hydromorphine | 3 | $1 \times 10^{-5}$ | 55 |
|  | 0.3 | $1 \times 10^{-5}$ | 6 |
| Thorazine | 35 | $9.9 \times 10^{-5}$ | 6 |
| Methadone | 30 | $8.7 \times 10^{-5}$ | 1 |
| Darvon | 300 | $8 \times 10^{-4}$ | 4 |
| Cocaine | 300 | $1 \times 10^{-3}$ | 2 |
| Pentazocine | 300 | $7.5 \times 10^{-4}$ | 3 |
| Phenobarbital | 300 | $1.2 \times 10^{-3}$ | 0 |

A total of 91 samples of patient urine were taken from a methadone clinic. All of the urine had been checked by thin layer chromatography, without hydrolysis, and four were found to contain morphine. Where morphine is present as the glucuronide it is not detected by the chromatographic system normally employed. The urines were then tested, both by FRAT ® spin label assay and the subject enzyme assay. Of the 91 samples, both the FRAT ® spin label assay and the subject enzyme assay showed the same 17 samples to be positive, which included the four positive samples found by thin layer chromatography. The amounts of morphine detected varied from a low of about 0.3μg/ml to a high of about 14.3μg/ml.

The next ligand to be considered is methadone. The methadone lysozyme conjugate was employed in the normal assay for lysozyme. The following table indicates the results from the cross-reactivity study. The results are reported as relative reactivity to methadone at 0.5μg/ml. That is, the relative activity is the ratio of the concentration of the drug in question to the concentration of methadone necessary to give the same optical density reading. The smaller the relative reactivity, the less reactivity the compound has in the assay. While the large number of compounds were studied, only a few compounds showed any response. The following table indicates the results.

METHADONE CROSS-REACTIVITY

| Compound: | Relative Reactivity |
|---|---|
| Methadone | 1 |
| Chlorpromazine | 0.011 |
| Dextromethorphan | 0.0042 |
| Dextropropoxyphene | 0.00089 |
| Phenergan | 0.0125 |

A group of 12 urines was collected from known heroin addicts. The urines were all shown to be positive morphine and negative methadone by thin layer chromatography. However, when the urines were assayed by the FRAT ® spin label assay method as well as by the subject enzyme method, both of these immunoassay techniques agreed on the presence of methadone in threa of the samples, as well as the positive presence of morphine in all the samples. When 100 samples were taken from a methadone clinic, there was 100% agreement between the FRAT ® spin label method and the enzyme immunoassay method as far as positive or negative for the presence of methadone and substantially good quantitative agreement between the determinations by the two different methods.

The next drug to be considered is amphetamine. Again, the same procedure is employed for lysozyme as for the prior assays, except that 50μl of urine is employed. The relative reactivity is related to 1μg/ml amphetamine.

AMPHETAMINE CROSS-REACTIVITY

| Compound: | Relative Reactivity |
|---|---|
| Amphetamine | 1 |
| Methamphetamine | 1.1 |
| Mephentermine, phentermine | 0.62 |
| Propylhexedrine | 0.05 |
| Phenethylamine | 0.2 |
| Cyclopentamine | 0.33 |
| Ephedrine | 0.22 |
| Phenylpropanolamine | 0.33 |
| Nylidrin | 0.27 |
| Isoxsuprine | 0.2 |
| p-Hydroxyamphetamine | 0.022 |

A series of urine samples were obtained which were verified to contain amphetamine by gas-liquid chromatography. The samples were then assayed by both the FRAT ® spin label assay and the subject enzyme assay. Excellent quantitative agreement was obtained between the FRAT ® spin label assay and the subject amphetamine assay.

It is found that phenylpropanolamine which has a relatively high relative reactivity is available in over-the-counter prescriptions. In order to avoid false positives, when a positive result is obtained from a urine, the urine is treated with sodium periodate and tetramethyl ammonium hydroxide for a few minutes at ambient temperatures. The pH of the urine should be in the range of about 8 to 9. This treatment is effective in removing phenylpropanolamine as an interferant. The other compounds which cross-react are not of a sufficient occurrence to be of substantial concern.

A barbiturate assay was carried out by combining antibodies to phenobarbital and secobarbital and the lysozyme conjugate prepared as described in Example 6. The phenobarbital-lysozyme conjugate (11μl, 1.066 $\times 10^{-5}$M) was combined with 4.65μl (1.89 $\times 10^{-5}$M) of the secobarbital-lysozyme conjugate, 5μl of a one percent BSA in pH 6.0 tris-maleate 0.025M buffer to provide 50μl of reagent with a maximum rate of ≃300

OD/min. (enzyme units). The antibody solution was prepared by combining 22.8µl of phenobarbital antibody (1.03 × 10⁻⁵M based on binding sites) with 15.4µl of secobarbital antibody (1.14 × 10⁻⁵M based on binding sites) and 11.8µl of pH 7.4 tris-maleate 0.025M buffer.

The assay for lysozyme was carried out in the conventional manner, employing 50µl of urine.

A group of 21 barbiturate positive urine samples were collected and analyzed by thin layer chromatography (TLC), gas-liquid chromatography (GLC), FRAT® spin label assay and the subject enzyme assay technique. The results obtained showed the excellent qualitative and quantitative correlation between the various methods. The combined enzyme assay is sensitive to 0.5µg/ml of secobarbital with somewhat less sensitivity to other barbiturates.

The use of lysozyme as the enzyme in a homogeneous enzyme immunoassay has numerous advantages. Lysozyme is a stable enzyme which has only a few lysine groups and of these, not all are susceptible to substitution. Thus, with only a few haptens conjugated to the enzyme, high degrees of inhibition can be obtained when the lysozyme conjugate is introduced into an excess of antibody for the particular hapten which is conjugated.

Lysozyme has a large substrate, namely bacterial cell walls, which when lysed, substantially change the amount of light which is transmitted through the sample. When the haptenic molecule competes with the conjugated hapten for antibody, small changes in haptenic concentration will result in significant changes in the activity of the enzyme present in the solution. Thus, one can obtain relatively large changes in light transmission with very low concentrations of haptens present in the sample solution.

Because of lysozyme's stability, it can be readily conjugated and retain a substantial proportion of its original activity. In addition, it has good storage life and is readily shipped. The enzyme is absent from many physiological fluids, so that these fluids can be studied without having large background results which would diminish the sensitivity of the assay.

Although the foregoing invention has been described in some detail by way of illustration and example for purposes of clarity of understanding, it will be obvious that certain changes and modifications may be practiced within the scope of the appended claims.

What is claimed is:

1. An enzyme conjugate of lysozyme of the formula:

LYS (X—R—Y)$_n$ wherein:
  LYS intends lysozyme;
  $n$ is the average number of groups bonded to the LYS and is in the range of 1 to 5;
  X is a bond or non-oxocarbonyl, including the nitrogen and sulfur analogs thereof;
  R is a linking group of from 1 to 12 carbon atoms and 0 to 3 heteroatoms which are oxygen, sulfur or nitrogen; and
  Y is a hapten of at least 125 molecular weight and not greater than about 1,200 molecular weight.

2. An enzyme conjugate according to claim 1, wherein $n$ is of from 2 to 5, X is a non-oxocarbonyl group, R is of from 1 to 4 carbon atoms and 0 to 2 heteroatoms, and Y is a hapten of from about 125 to about 650 molecular weight.

3. An enzyme conjugate according to claim 1, wherein R is aliphatic having from 0 to 1 site of ethylenic unsaturation.

4. An enzyme conjugate according to claim 3, wherein R is of from 1 to 4 carbon atoms and 0 to 2 heteroatoms.

5. An enzyme conjugate according to claim 1, wherein R is arylene or diazoarylene, with the proviso that when R is diazoarylene, X is a bond.

6. An enzyme conjugate according to claim 1, wherein X is non-oxo-carbonyl, $n$ is 2 to 5, and R is an aliphatic linking group of from 1 to 8 carbon atoms and 0 to 3 heteroatoms which are of atomic number 7 to 8.

7. An enzyme conjugate of the formula:

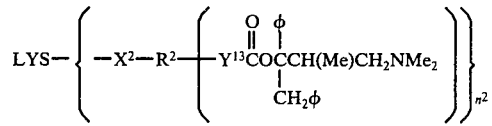

wherein:
  LYS is lysozyme.
  $X^2$ is a bond or non-oxo-carbonyl group including the nitrogen and sulfur analogs thereof;
  $R^2$ is aliphatic of from 1 to 4 carbon atoms;
  $n^2$ is the average number of groups bonded to the LYS and is in the range of 2 to 5; and
  $Y^{13}$ is a bond.

8. An enzyme conjugate of the formula:

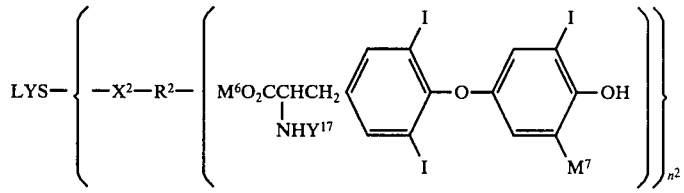

wherein:
  LYS is lysozyme,
  $X^2$ is a bond or non-oxo-carbonyl group, including the nitrogen and sulfur analogs thereof;
  $R^2$ is an aliphatic group of from 1 to 6 carbon atoms, and from 1 to 2 heteroatoms which are of atomic number 7 to 8 and is bonded to nitrogen through carbonyl;
  $M^6$ is hydrogen or lower alkyl of from 1 to 6 carbon atoms;
  $M^7$ is hydrogen or iodo;
  $Y^{17}$ is a bond, and
  $n^2$ is the average number of groups bonded to the LYS and is in the range of 2 to 5.

9. An enzyme conjugate of the formula:

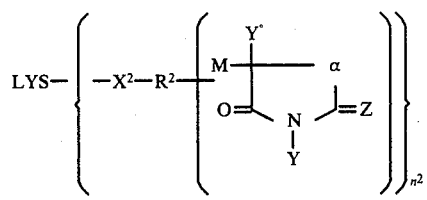

wherein:

LYS is lysozyme;

$X^2$ is a bond or non-oxo-carbonyl, including the nitrogen and sulfur analogs thereof;

$R^2$ is an aliphatic group of from 1 to 4 carbon atoms;

$\alpha$ is ethylene;

$n^2$ is the average number of groups bonded to the LYS and is in the range of 2 to 5;

Z is oxygen;

M is phenyl; and one of Y and Y° is a bond, and when other than a bond, Y is hydrogen and Y° is lower alkyl of from 1 to 3 carbon atoms.

10. A lysozyme conjugate having from 1 to 5 haptens of molecular weight in the range of about 125 to 1200, wherein upon addition of antibody for said haptens to said lysozyme conjugate the enzyme activity of said lysozyme is substantially reduced when said haptens are bound to antibody.

11. A lysozyme conjugate according to claim 10, having from 2 to 5 haptens.

12. A lysozyme conjugate according to claim 10, wherein said lysozyme conjugate has at least about 50 percent of the lysozyme activity prior to conjugation.

* * * * *